(12) United States Patent
Lee

(10) Patent No.: US 8,794,109 B2
(45) Date of Patent: Aug. 5, 2014

(54) TATTOOING APPARATUS

(76) Inventor: Jong-Dae Lee, Seoul (KR)

(*) Notice: Subject to any disclaimer, the term of this patent is extended or adjusted under 35 U.S.C. 154(b) by 1158 days.

(21) Appl. No.: 12/376,332

(22) PCT Filed: Aug. 13, 2007

(86) PCT No.: PCT/KR2007/003874
§ 371 (c)(1),
(2), (4) Date: Apr. 2, 2010

(87) PCT Pub. No.: WO2008/018781
PCT Pub. Date: Feb. 14, 2008

(65) Prior Publication Data
US 2010/0191268 A1 Jul. 29, 2010

(30) Foreign Application Priority Data
Aug. 11, 2006 (KR) .................. 10-2006-0076338

(51) Int. Cl.
*B43K 5/00* (2006.01)
*A61B 17/34* (2006.01)

(52) U.S. Cl.
USPC ......................................... 81/9.22

(58) Field of Classification Search
USPC .................. 81/9.22; 606/185, 186
See application file for complete search history.

(56) References Cited

U.S. PATENT DOCUMENTS

| 1,859,457 | A | * | 5/1932 | Newhouse ............... 74/569 |
| 4,719,825 | A | * | 1/1988 | LaHaye et al. ........... 81/9.22 |
| 4,796,624 | A | * | 1/1989 | Trott et al. ............... 606/185 |
| 4,914,988 | A | * | 4/1990 | Chang ..................... 81/9.22 |
| 5,471,102 | A | * | 11/1995 | Becker et al. ............ 310/50 |
| 2003/0195542 | A1 | * | 10/2003 | Lee ........................... 606/186 |
| 2008/0228214 | A1 | * | 9/2008 | Hoan et al. ............... 606/185 |
| 2008/0287978 | A1 | * | 11/2008 | Hickman, III ........... 606/186 |

FOREIGN PATENT DOCUMENTS

| DE | 202004016876 U1 | 8/2005 |
| EP | 1495782 B1 | 1/2005 |
| JP | 01-131428 U | 9/1989 |
| KR | 20-1988-0001981 U | 4/1988 |
| KR | 10-2003-0080664 A | 10/2003 |

* cited by examiner

*Primary Examiner* — David B Thomas
*Assistant Examiner* — Danny Hong
(74) *Attorney, Agent, or Firm* — Cantor Colburn LLP

(57) ABSTRACT

The present invention relates to a tattooing apparatus having a tattooing needle capable of automatically reciprocating in a linear direction. The tattooing apparatus according to the present invention includes a case, a motor disposed inside the case, a cam unit to convert rotation of the motor into linear reciprocation, a link connected to the cam unit and disposed inside the case to be linearly reciprocated by the cam unit, and a needle cartridge that is connected to a lower end of the case and has a tattooing needle to move according to the link and a tattooing ink to flow out along the tattooing needle.

5 Claims, 5 Drawing Sheets

TATTOOING APPARATUS

TECHNICAL FIELD

The present invention relates to a tattooing apparatus. More particularly, the present invention relates to a tattooing apparatus formed so that a tattooing needle can automatically reciprocate in a linear direction.

BACKGROUND ART

Generally, a tattooing apparatus is an apparatus that uses tattooing ink and a tattooing needle to draw pictures and/or marks such as symbols, letters, diagrams, etc. on a human's skin.

For convenience of tattooing, a conventional tattooing apparatus is configured so that a tattooing needle automatically reciprocates back and forth and tattooing ink flows out along the tattooing needle when the tattooing needle reciprocates. Therefore, a tattoo artist forces the tattooing needle to insert into a skin of a person to be tattooed in a predetermined depth and to move, thereby forming marks or pictures on the skin of the person according to his/her intention.

However, the conventional tattooing apparatus is provided with an ink-storing portion, which stores a predetermined amount of tattooing ink to flow out when the tattooing needle reciprocates, in a body portion that supports the tattooing needle to reciprocate. Also, an ink hole through which the tattooing ink is supplied to the ink-storing portion is formed on an outer circumferential surface of the body portion. The ink hole has substantially the same diameter as that of the body portion. Therefore, the tattoo artist supplies tattooing ink to the ink-storing portion via the ink hole to fill up the ink-storing portion before tattooing. However, since, in the conventional tattooing apparatus, the ink hole, through which the tattooing ink is supplied to the ink-storing portion, has a rather large diameter and is directly exposed to the outside, even when the body portion of the tattooing apparatus is slightly inclined, the tattooing ink stored in the ink-storing portion may flow over through the ink hole. Therefore, it is very inconvenient to use the conventional tattooing apparatus to perform a tattooing work.

Also, because the tattooing needle of the conventional tattooing apparatus cannot reciprocate in a linear direction, when performing the tattooing work, although the tattoo artist forces the tattooing needle to vertically insert into the skin of the person to be tattooed, the tattooing needle comes out the skin at a predetermined angle with respect to a line perpendicular to the skin. In other words, an advance trace of the tattooing needle is different from a withdraw trace of the tattooing needle. Therefore, when tattooing, the person to be tattooed feels a bad pain, the skin of the person is damaged.

Furthermore, the conventional tattooing apparatus is configured to use a motor to advance the tattooing needle to project, and a spring to withdraw the projected tattooing needle. As a result, when the spring loses elasticity thereof due to a long-term usage, the projected tattooing needle may not be withdrawn, or it takes time for the projected tattooing needle to be withdrawn. If the tattooing needle cannot precisely reciprocate as described above, the tattoo artist feels difficult to tattoo precisely.

DISCLOSURE OF INVENTION

Technical Problem

The present invention has been developed in order to overcome the above drawbacks and other problems associated with the conventional arrangement. An aspect of the is to provide a tattooing apparatus having a tattooing needle that is driven to reciprocate in a linear direction by a motor.

Another aspect of the present invention is to provide a tattooing apparatus that can minimize vibration and noise to generate when a tattooing needle is reciprocated in a linear direction by a motor.

Another aspect of the present invention is to provide a tattooing apparatus which tattooing ink does not flow over during a tattooing.

Technical Solution

The above aspects and/or other features of the present invention, which includes a case; a motor disposed inside the case; a cam unit to convert a rotational movement of the motor into a linear reciprocating movement; a link connected to the cam unit and disposed inside the case to be linearly reciprocated by the cam unit; and a needle cartridge that is connected to a lower end of the case, and has a tattooing needle to move according to the link and tattooing ink to flow out along the tattooing needle. The cam unit includes a cam formed substantially in a circular plate shape, a top surface of which is parallel to the tattooing needle, the cam to have a cam groove formed substantially in a circle eccentric with respect to a rotation center of the cam on the top surface of the cam, and the cam formed so that when the cam is rotated by the motor, the center of the gravity of the cam is not changed with respect to the rotation center; and a cam follower to have one end thereof inserted into the cam groove and the other end thereof fixed to the link, and the cam follower to reciprocate linearly when the cam rotates; wherein a contacting point of the cam follower and the cam groove is substantially aligned with the tattooing needle.

The needle cartridge may include a cartridge body connected the case, to include an ink-storing portion to store the tattooing ink and formed in a substantially cylindrical shape with a close outer circumferential surface; a needle holder in which the tattooing needle is disposed, to reciprocate linearly inside the ink-storing portion; a slider disposed to connect the needle holder and the link, and reciprocate linearly with respect to the cartridge body; and a needle tip disposed at a front end of the cartridge body and to support the tattooing needle to reciprocate linearly.

A hooking protrusion may be formed at one end of the slider. The link may be provided with a guiding hole to guide the hooking protrusion and a holding groove on which the hooking protrusion is hooked in one end of the link to which the slider is connected.

The needle holder may contact closely and move along an inner surface of the cartridge body so as to suck the tattooing ink via the needle tip.

Advantageous Effects

In the tattooing apparatus according to an embodiment of the present invention as described above, the cam unit operated by the motor causes the tattooing needle to reciprocate linearly so that the tattooing needle can exactly reciprocate in a linear motion. As a result, when tattooing, the skin of the person to be tattooed cannot be damaged and pain of the person to be tattooed can be decreased.

Also, the cam unit forcibly advances and withdraws the tattooing needle so that the tattooing needle can exactly reciprocate in a linear motion. Therefore, the tattoo artist can precisely tattoo.

Also, since the tattooing apparatus according to the present invention can suck tattooing ink via the needle tip, it does not need to have a separate ink hole for supplying tattooing ink. Therefore, the tattooing ink does not flow over the ink hole during tattooing so that it is very convenient to tattoo.

Furthermore, in the tattooing apparatus according to the present invention, the cam and cam follower of the cam unit that converts the rotational movement of the motor into the linear reciprocation movement are arranged to be substantially aligned with the tattooing needle so that when the cam and the cam follower operate, the center of gravity thereof does not change. Also, the cam is formed to have a substantially regular weight based on the rotation center thereof so that when the cam rotates, the center of gravity of the cam is almost not changed with respect to the rotation center of the cam. As a result, when the cam unit converts the rotational movement of the motor into the linear reciprocating movement, the tattooing apparatus does almost not vibrate. Therefore, the tattooing work may be not disturbed by vibration of the tattooing apparatus.

BEST MODE FOR CARRYING OUT THE INVENTION

Hereinafter, certain exemplary embodiments of the present invention will be described in detail with reference to the accompanying drawings. The matters defined in the description, such as a detailed construction and elements thereof, are provided to assist in a comprehensive understanding of the invention. Thus, it is apparent that the present invention may be carried out without those defined matters. Also, well-known functions or constructions are omitted to provide a clear and concise description of exemplary embodiments of the.

Figure 1:
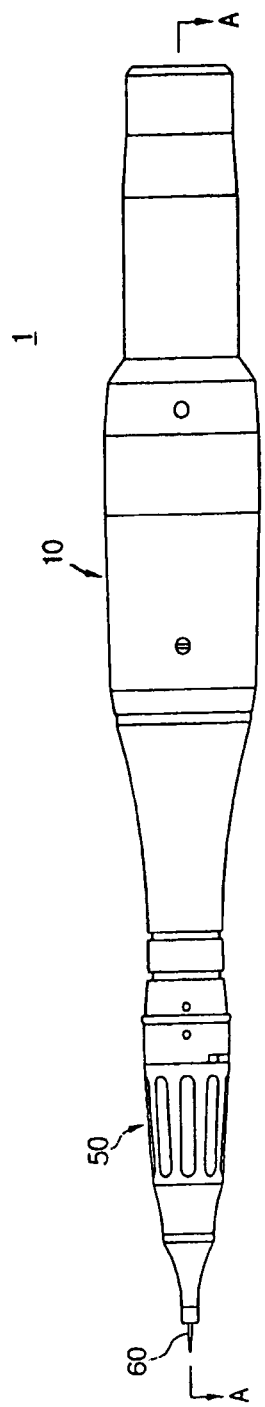
FIG. 1 is a front view illustrating a tattooing apparatus according to an embodiment of the present invention.
Figure 2:
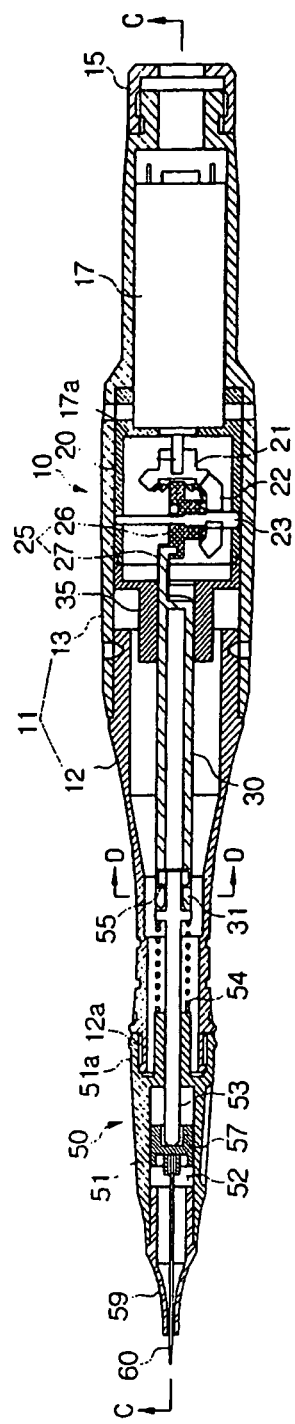
FIG. 2 is a sectional view illustrating the tattooing apparatus of FIG. 1 taken along a line A-A in FIG. 1.
Figure 3:
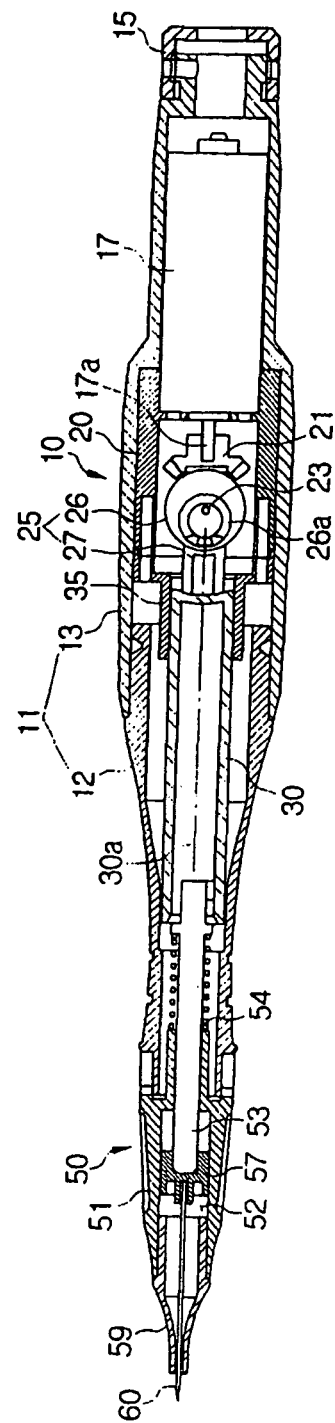
FIG. 3 is a sectional view illustrating the tattooing apparatus of FIG. 2 taken along a line C-C in FIG. 2.

Referring to FIGS. 1 to 3, a tattooing apparatus 1 according to an embodiment of the present invention includes a main body 10, and a needle cartridge 50.

The main body 10 includes a case 11, a motor 17, a cam unit 25, and a link 30. The case 11 forms an appearance of the tattooing apparatus 1, and supports and fixes the motor 17, the cam unit 25, and the link 30. The case 11 may be formed in a single body. However, for convenience of assembly, the case 11 may be formed to have an upper case 12 and a lower case 13. The needle cartridge 50 is connected to a front end 12a of the upper case 12. At this time, the connection of the upper case 12 and the needle cartridge 50 may be formed to use one-touch connection and disconnection method. For example, a connecting groove is formed at a rear end 51a of the needle cartridge 50, and a projection corresponding to the connecting groove is formed at the front end 12a of the upper case 12. Then, the projection of the front end 12a of the upper case 12 is inserted into and rotated in a predetermined angle with respect to the connecting groove of the rear end 51a of the needle cartridge 50 so that the needle cartridge 50 is connected to the upper case 12. For disconnection of them, the needle cartridge 50 is rotated by the same angle in a reverse direction and pulled out, thereby being separated from the upper case 12. In addition to the above-described method, various well-known one-touch connection and disconnection methods can be used to connect the needle cartridge 50 to the upper case 12. Also, a cable cap 15 to hold an electric cable (not illustrated) connected to the motor 17 is disposed at a rear end of the lower case 13.

The motor 17 is disposed inside the lower case 13, and connected with the electric cable to receive electric power supplied from outside.

The cam unit 25 converts the rotational movement of the motor 17 into a linear reciprocating movement, and includes a cam 26 and a cam follower 27. The cam 26 may be formed substantially in a circular plate shape, and receives power from the motor 17 to rotate. A cam groove 26a is formed substantially in a circle on a top surface of the cam 26. The cam groove 26a is eccentric with respect to a rotation center of the cam 26, that is, a rotation shaft 23. One end of the cam follower 27 is inserted into the cam groove 26a, and the other end of the cam follower 27 is fixed to the link 30. Therefore, when the cam 26 rotates, the cam follower 27 inserted into the cam groove 26a moves along the cam groove 26a so that the rotational movement of the cam 26 is converted into the linear reciprocating movement of the cam follower 27.

At this time, the cam 26 and the cam follower 27 may be arranged as illustrated in FIG. 2 so that the cam follower 27 can move parallel to the top surface of the cam 26. Then, a contacting point on which the cam follower 27 contacts the cam groove 26a of the cam 26 is substantially aligned with a shaft 17a of the motor 17, a slider 53 of the needle cartridge 50, and a tattooing needle 60. In detail, a moving trace that the contacting point between the cam groove 26a and the cam follower 27 forms when the cam 26 rotates, that is, a trace along which the cam follower 27 reciprocates linearly is substantially aligned with the shaft 17a of the motor 17, the slider 53 of the needle cartridge 50, and the tattooing needle 60. In other words, the trace of the cam follower 27 is located substantially in a straight line that the shaft 17a of the motor 17, the slider 53 of the needle cartridge 50, and the tattooing needle 60 form. As a result, even when the cam 26 rotates, the center of gravity of the cam unit 25 is almost not changed with respect to the straight line to join the shaft 17a of the motor 17 and the tattooing needle 60.

Also, the cam 26 may be formed to have a substantially regularly distributed weight with respect to the rotation shaft 23. If the cam 26 is formed as described above, when the cam 26 rotates, the center of gravity of the cam 26 is almost not changed with respect to the rotation shaft 23 to form the rotation center of the cam 26.

In other words, in the tattooing apparatus 1 according to an embodiment of the present invention, as described above, the cam unit 25 is disposed so that when the cam 26 rotates, the center of gravity of the cam unit 25 is almost not changed with respect to not only the rotation center 23 of the cam 26 but also the straight line to join the shaft 17a of the motor 17 and the tattooing needle 60. Therefore, when the rotational movement of the motor 17 is converted into the linear reciprocating movement by the cam 26 and cam follower 27 of the cam unit 25, the main body 10 does not vibrate. Especially, even when high-speed motors (for example, a rotation number of 500~4,000 rpm (revolutions per minute)) are used as the motor 17, vibration and noise to cause troubles are not generated.

On the other hand, the cam 26 may be rotated by a pair of bevel gears 21 and 22 as illustrated in FIGS. 2 and 3 so that the motor 17, the cam 26, and the cam follower 27 can be arranged substantially in a straight line together with the needle cartridge 50. Also, a holder 20 may be disposed to support the rotation of the cam 26 and the second bevel gear 22 for convenience of assembly. Therefore, the cam 26 and the second bevel gear 22 are coaxially disposed on the rotation shaft 23 that is rotatably disposed at the holder 20.

Figure 4:
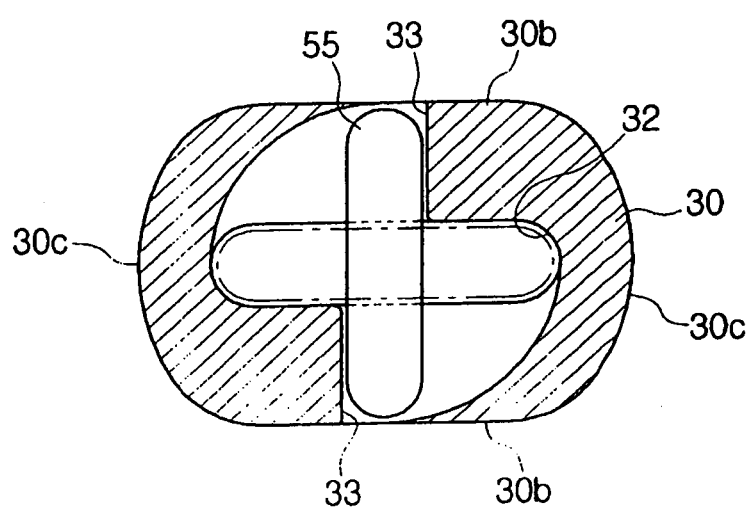
FIG. 4 is a partial sectional view illustrating a connection between link and slider of the tattooing apparatus of FIG. 2 taken along a line D-D in FIG. 2.
Figure 5:
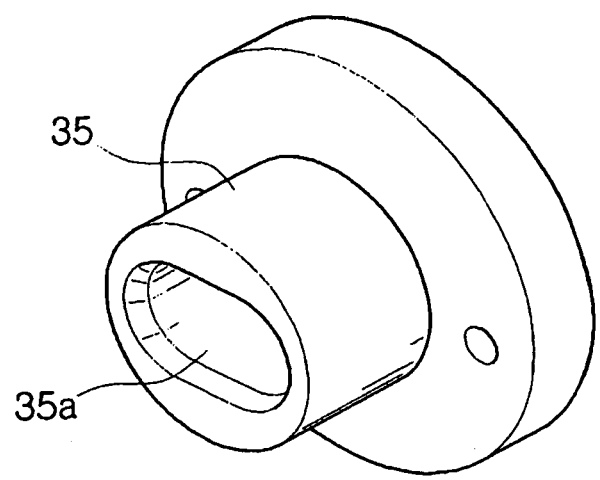
FIG. 5 is a perspective view illustrating a guide member of the tattooing apparatus of FIG. 2.

The link 30 is disposed to be connected to the cam unit 25, and reciprocated linearly inside the case 11 by the cam unit 25. That is, one end of the link 30 is connected to the cam follower 27 of the cam unit 25 so that the linear reciprocating movement of the cam follower 27 causes the link 30 to reciprocate linearly. At this time, the cam follower 27 may be formed integrally with the link 30. Also, the link 30 may be formed to have a non-circular section so as to prevent the link 30 from rotating on a lengthwise axis 30a of the link 30 during the linear reciprocating movement of the link 30. For example, the link 30 may have a non-circular section such as an oval, a rectangle, etc. In this embodiment, as illustrated in FIG. 4, the link 30 has a section formed so that top and bottom sides 30b thereof are parallel straight lines, and left and right sides 30c thereof are symmetrical arc shapes. Also, a connecting portion 31 is formed at a front end of the link 30, that is, an end of the link 30 to which the needle cartridge 50 is connected so that the link 30 is one-touch connected to the slider 53 of the needle cartridge 50. The connecting portion 31, as illustrated in FIG. 4, is provided with a guiding hole 32 through which a hooking protrusion 55 of the slider 53 can be inserted into the inside of the link 30, and a holding groove 33 on which the hooking protrusion 55 is hooked. Also, the lower case 13 is provided with a guide member 35 to guide the linear reciprocating movement of the link 30. The guide member 35, as illustrated in FIG. 5, is provided with a guide opening 35a corresponding to the section of the link 30.

The needle cartridge 50 is connected to the front or distal end 12a of the case 11, and includes the tattooing needle 60 disposed to advance and withdraw according to the movement of the link 30. The needle cartridge 50 also holds a predetermined amount of tattooing ink that flows out along the tattooing needle 60 when the tattooing needle 60 reciprocates linearly. The needle cartridge 50 includes a cartridge body 51, a needle holder 57, the slider 53, a needle tip 59, and the tattooing needle 60.

A rear end 51a of the cartridge body 51 is connected to the case 11, that is, the front end 12a of the upper case 12. An ink-storing portion 52 to store the tattooing ink is formed in a substantially cylindrical shape inside the cartridge body 51. Unlike the conventional tattooing apparatus, the cartridge body 51 does not have an ink hole that is separately formed to supply the tattooing ink to the ink-storing portion 52 therethrough. That is, an outer circumferential surface of the cartridge body 51 in a substantially cylindrical shape is closed except for the front end of the cartridge body 51 through which the tattooing needle 60 projects and the rear end 51a of the cartridge body 51 connected to the case 11. Therefore, during tattooing it is not occurred that the tattooing ink stored in the ink-storing portion 52 flows over. Also, the needle holder 57 is disposed inside the cartridge body 51, that is, inside the ink-storing portion 52 so that the needle holder 57 tightly contacts and reciprocates in a linear motion along an inner surface of the cartridge body 51.

The tattooing needle 60 is disposed at one side of the needle holder 57, and the slider 53 is disposed at the other side of the needle holder 57. Therefore, when the slider 53 reciprocates linearly, the needle holder 57 reciprocates linearly inside the ink-storing portion 52 as a piston, thereby discharging or sucking the tattooing ink.

The slider 53 is disposed to connect the needle holder 57 and the link 30, and to reciprocate linearly with respect to the cartridge body 51. The hooking protrusion 55 is formed at the rear end of the slider 53, that is, the portion connected to the link 30. Therefore, when the hooking protrusion 55 of the slider 53 is inserted into the guiding hole 32 of the link 30, and turned by approximately 90 degrees, the hooking protrusion 55 of the slider 53 is hooked on the holding groove 33 of the link 30 so that the slider 53 does not come out in an axial direction. When separating, the slider 53 is turned in the reverse direction, and pulled out. In other words, the slider 53 is connected to the link 30 by the one-touch connection method. At this time, the hooking protrusion 55 of the slider 53 may be formed to coincide with a direction of the connecting groove of the cartridge body 51 so that when the cartridge body 51 is turned in a direction, the projection of the upper case 12 is hooked on the connecting groove of the cartridge body 51, and the hooking protrusion 55 of the slider 53 is hooked on the holding groove 33 of the link 30.

The needle tip 59 is disposed at the front end of the cartridge body 51, and supports the tattooing needle 60 to smoothly reciprocate in a linear motion. Also, when the tattooing needle 60 reciprocates, the tattooing ink flows out between the needle tip 59 and the tattooing needle 60.

The tattooing needle 60 is advanced and withdrawn with respect to the needle tip 59 by the linear reciprocating movement of the needle holder 57. Therefore, when the needle holder 57 advances, the tattooing needle 60 is advanced to project from of the front end of the needle tip 59. When the needle holder 57 withdraws, the tattooing needle 60 is withdrawn to locate inside the needle tip 59.

Also, a spring 54 may be disposed between the rear end of the cartridge body 51 and the hooking protrusion 55 of the slider 53 so as to assist the linear reciprocating movement of the slider 53 and to maintain the stable connection between the slider 53 and the link 30.

Hereinafter, operation of the tattooing apparatus 1 according to an embodiment of the present invention having the structure as described above will be explained in detail with reference to the accompanying drawings.

First, the case will be explained when the needle cartridge 50 is connected to the main body 10.

After the hooking protrusion 55 of the slider 53 is aligned with and pushed into the guiding hole 32 of the link 30, the slider 53 is turned by a predetermined angle in one direction. So, the hooking protrusion 55 is hooked on the holding groove 33 so that the slider 53 does not come out in the axial direction of the link 30. At the same time, the projection of the upper case 12 is inserted along and fixed to the connecting groove of the cartridge body 51. That is, the cartridge body 51 of the needle cartridge 50 is fixed to the case 11 of the main body 10, and the slider 53 of the needle cartridge 50 is fixed to the link 30.

Next, the case will be explained when a tattooing work is performed using the tattooing apparatus 1 with the needle cartridge 50 according to an embodiment of the present invention.

When the motor 17 is turned on to rotate, the first bevel gear 21 disposed on the shaft 17a of the motor 17 rotates. Then, the second bevel gear 22 engaged with the first bevel gear 21 rotates. When the second bevel gear 22 rotates, the cam 26 disposed coaxially with the second bevel gear 22 on the rotation shaft 23 rotates. When the cam 26 rotates, the cam groove 26a formed on the cam 26 rotates eccentrically on the rotation shaft 23. As a result, the cam follower 27 inserted into the cam groove 26a is reciprocated linearly by the cam groove 26a. Accordingly, when a center of the cam groove 26a locates at a lower side of the rotation shaft 23 as illustrated in FIGS. 2 and 3, the cam follower 27 is moved to the lower side. When the cam follower 27 moves to the lower side, the link 30, the slider 53, and the needle holder 57 are totally moved to the lower side so that the tattooing needle 60 is advanced to project from the front end of the needle tip 59. After that, when the cam 26 continues to rotate so that the center of the cam groove 26a locates at an upper side of the rotation shaft 23, the cam follower 27 is moved toward the upper side. When the cam follower 27 moves toward the upper side, the link 30, the slider 53, and the needle holder 57 are totally moved toward the upper side so that the tattooing needle 60 is withdrawn to locate inside the needle tip 59. When the tattooing needle 60 reciprocates linearly with respect to the needle tip 59, the tattooing ink flows out along the tattooing needle 60 from the ink-storing portion 52 and enters a skin of a person to be tattooed. As described above, the tattooing needle 60 is reciprocated linearly by the cam 26 and the cam follower 27 so that a trace along which the tattooing needle 60 advances is substantially the same as that along which the tattooing needle 60 withdraws. As a result, when tattooing using the tattooing apparatus 1 according to an embodiment of the present invention, the skin of the person to be tattooed is not damaged, and the person to be tattooed does not feel serious pain. Also, the tattooing needle 60 is forcibly advanced and withdrawn by the cam unit 25 so that the tattooing needle 60 can precisely reciprocate in the linear motion. Furthermore, the moving trace that the contacting point of the cam groove 26a and the cam follower 27 forms is substantially aligned with the tattooing needle 60 so that when the cam unit 25 converts the rotational movement of the motor 17 into the linear reciprocating movement of the tattooing needle 60, vibration to disturb the tattooing work does not occur.

When filling up the needle cartridge 50 with the tattooing ink, the motor 17 is operated in a state that the front end of the needle tip 59 is submerged in the tattooing ink of an inkbottle. Then, the cam unit 25 causes the needle holder 57 to reciprocate linearly as a piston inside the ink-storing portion 52. When the needle holder 57 reciprocates linearly inside the ink-storing portion 52, the tattooing ink is sucked into the ink-storing portion 52 along the tattooing needle 60 to reciprocate linearly at the front end of the needle tip 59. That is, the needle holder 57 to reciprocate linearly sucks the tattooing ink into the ink-storing portion 52. As a result, even though the needle cartridge 50 does not have the ink hole, the tattooing apparatus 1 according to an embodiment of the present invention can fill up the ink-storing portion 52 with the tattooing ink.

After the tattooing work of one person to be tattooed finishes, the needle cartridge 50 is separated from the main body 10 and thrown away. When tattooing, blood of the person to be tattooed may be sucked into the ink-storing portion 52 along the tattooing needle 60. So, when another person is tattooed using the same needle cartridge 50, the sucked blood may infect him/her. Therefore, using a disposable needle cartridge 50 can prevent the infection accident from occurring. When separating the needle cartridge 50 from the main body 10, the needle cartridge 50 is turned by approximately 90 degrees in an opposite direction to which the needle cartridge 50 is connected to the main body 10 and pulled out, thereby easily being separated from the main body 10.

While the embodiments of the present invention have been described, additional variations and modifications of the embodiments may occur to those skilled in the art once they learn of the basic inventive concepts. Therefore, it is intended that the appended claims shall be construed to include both the above embodiments and all such variations and modifications that fall within the spirit and scope of the invention.

The invention claimed is:

1. A tattooing apparatus comprising:
   a case;
   a motor disposed inside the case;
   a cam unit to convert a rotational movement of the motor into a linear reciprocating movement;
   a link connected to the cam unit and disposed inside the case to be linearly reciprocated by the cam unit; and
   a needle cartridge connected to a distal end of the case, and having a tattooing needle to linearly move in response to movement the link and tattooing ink to flow out along the tattooing needle;
   wherein the cam unit comprises;
      a cam having a substantially circular plate shape, the cam including a planar top surface which is parallel to a longitudinal axis of the tattooing needle, and a cam groove formed on the planar top surface of the cam, the cam groove having a substantially circular shape eccentric with respect to a rotation center of the cam; and
      a cam follower having a first end thereof inserted into the cam groove for cam contact, with its contact point substantially aligned with the longitudinal axis of the tattooing needle, and a second end thereof fixed to the link, and the cam follower reciprocating linearly when the cam rotates.

2. The tattooing apparatus of claim 1, wherein the needle cartridge comprises;
   a cartridge body connected the case and having an ink-storing portion to store the tattooing ink, the cartridge body having a substantially cylindrical shape with a close outer circumferential surface;
   a needle holder to which the tattooing needle is connected, the needle holder reciprocating linearly inside the ink-storing portion;
   a slider disposed to connect the needle holder and the link, and reciprocating linearly with respect to the cartridge body; and
   a needle tip disposed at a front end of the cartridge body and to support the tattooing needle to reciprocate linearly.

3. The tattooing apparatus of claim 2, wherein a hooking protrusion is formed at one end of the slider, and the link is provided with a guiding hole to guide the hooking protrusion and a holding groove on which the hooking protrusion is hooked in one end of the link to which the slider is connected.

4. The tattooing apparatus of claim 2, wherein the needle holder contacts tightly and moves along an inner surface of the cartridge body so as to suck the tattooing ink via the needle tip.

5. The tattooing apparatus of claim 1, further comprising a pair of bevel gears coupled between the motor and the cam.

* * * * *